(12) United States Patent
Morell et al.

(10) Patent No.: US 6,902,796 B2
(45) Date of Patent: Jun. 7, 2005

(54) ELASTIC STRAND BONDED LAMINATE

(75) Inventors: Charles Morell, Roswell, GA (US); James Russell Fitts, Jr., Gainesville, GA (US); Bryan D. Haynes, Cumming, GA (US); Leslie D. Dobbins, Marietta, GA (US); Donald V. Willitts, Douglasville, GA (US); Stephen Michael Campbell, Winneconne, WI (US); Howard Martin Welch, Woodstock, GA (US); Todd Christopher Larson, Appleton, WI (US); Mark Michael Mleziva, Appleton, WI (US); Adrian Roy Eggen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 213 days.

(21) Appl. No.: 10/034,335

(22) Filed: Dec. 28, 2001

(65) Prior Publication Data

US 2003/0124331 A1 Jul. 3, 2003

(51) Int. Cl.[7] .............................................. B32B 27/04
(52) U.S. Cl. ................................ 428/292.1; 428/297.1; 428/299.1; 428/373; 428/411.1
(58) Field of Search ...................... 428/292.4, 190, 428/373, 297.1, 299.7, 222, 370, 411.1, 192, 193, 176; 442/394, 400, 398, 52, 329

(56) References Cited

U.S. PATENT DOCUMENTS

| | | | |
|---|---|---|---|
| 2,206,761 A | 7/1940 | Bergstein | |
| 2,266,761 A | 12/1941 | Jackson, Jr. et al. | |
| 2,357,392 A | 9/1944 | Francis, Jr. | |
| 2,464,301 A | 3/1949 | Francis, Jr. | |
| 2,483,405 A | 10/1949 | Francis, Jr. | |
| 2,957,512 A | 10/1960 | Wade et al. | |
| 2,957,852 A | 10/1960 | Frankenburg et al. | |
| 3,186,893 A | 6/1965 | Mercer | |
| 3,338,992 A | 8/1967 | Kinney | 264/24 |
| 3,341,394 A | 9/1967 | Kinney | 161/72 |
| 3,371,668 A | 3/1968 | Johnson | |
| 3,391,048 A | 7/1968 | Dyer et al. | |
| 3,439,085 A | 4/1969 | Hartmann | |
| 3,449,187 A | 6/1969 | Bobkowicz | |
| 3,468,748 A | 9/1969 | Bassett | |

(Continued)

FOREIGN PATENT DOCUMENTS

| | | | |
|---|---|---|---|
| CA | 2 165 486 | 6/1996 | |
| DE | 34 23 644 | 1/1986 | ........... A41B/13/02 |
| DE | 37 34 963 | 4/1988 | ........... C08L/21/00 |
| EP | 0 155 636 | 9/1985 | ........... A41B/13/02 |
| EP | 0 172 037 | 2/1986 | ........... A41B/13/02 |
| EP | 0 217 032 | 4/1987 | ........... D04H/13/00 |
| EP | 0 239 080 | 9/1987 | ............. D01F/6/30 |
| EP | 0 380 781 | 8/1990 | ............. B05C/5/02 |
| EP | 0 396 800 | 11/1990 | ........... A61F/13/56 |
| EP | 0 456 885 | 11/1991 | ........... A61F/13/15 |
| EP | 0 547 497 | 6/1993 | ........... A61F/13/15 |
| EP | 0 582 569 | 2/1994 | ............. B32B/5/26 |
| EP | 0 604 731 | 7/1994 | ........... B32B/31/00 |

(Continued)

Primary Examiner—Bruce H. Hess
Assistant Examiner—Camie S Tompson
(74) Attorney, Agent, or Firm—Pauley Petersen & Erickson (57) ABSTRACT

A simplified elastic laminate is made from nonwovens and is especially suitable for side panels of training pant garments or the like. A plurality of thermoplastic adhesive elastomeric fibers are located between first and second facing webs. The fibers have an elastic core and adhesive surfaces. The facing webs, with the elastomeric fibers between them, are calendered together thus adhering the facing webs together via contact adhesion with the elastomeric fibers.

16 Claims, 4 Drawing Sheets

U.S. PATENT DOCUMENTS

| | | | |
|---|---|---|---|
| 3,489,148 A | 1/1970 | Duncan et al. | |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,575,782 A | 4/1971 | Hansen | |
| 3,616,129 A | 10/1971 | Sager | |
| 3,629,047 A | 12/1971 | Davidson | |
| 3,669,823 A | 6/1972 | Wood | |
| 3,673,026 A | 6/1972 | Brown | |
| 3,676,242 A | 7/1972 | Prentice | |
| 3,689,342 A | 9/1972 | Vogt et al. | |
| 3,692,618 A | 9/1972 | Dorschner et al. | 161/72 |
| 3,752,613 A | 8/1973 | Vogt et al. | |
| 3,773,590 A | 11/1973 | Morgan | |
| 3,802,817 A | 4/1974 | Matsuki et al. | 425/66 |
| 3,806,289 A | 4/1974 | Schwarz | |
| 3,836,416 A | 9/1974 | Ropiequet | |
| 3,838,692 A | 10/1974 | Levesque | |
| 3,849,241 A | 11/1974 | Butin et al. | 161/169 |
| 3,857,144 A | 12/1974 | Bustin | |
| 3,860,003 A | 1/1975 | Buell | |
| 3,890,184 A | 6/1975 | Morgan | |
| 3,904,465 A | 9/1975 | Haase et al. | |
| 3,912,567 A | 10/1975 | Schwartz | |
| 3,917,448 A | 11/1975 | Wood | |
| 3,932,328 A | 1/1976 | Korpman | |
| 3,949,128 A | 4/1976 | Ostermeier | |
| 3,949,130 A | 4/1976 | Sabee et al. | |
| 3,973,063 A | 8/1976 | Clayton | |
| 3,978,185 A | 8/1976 | Buntin et al. | |
| 3,979,050 A | 9/1976 | Cilia | |
| 4,013,816 A | 3/1977 | Sabee et al. | |
| 4,028,292 A | 6/1977 | Korpman | |
| 4,038,346 A | 7/1977 | Feeney | |
| 4,080,348 A | 3/1978 | Korpman | |
| 4,090,385 A | 5/1978 | Packard | |
| 4,100,324 A | 7/1978 | Anderson et al. | 428/288 |
| 4,107,364 A | 8/1978 | Sisson | |
| 4,148,676 A | 4/1979 | Paquette et al. | |
| 4,189,338 A | 2/1980 | Ejima et al. | 156/167 |
| 4,209,563 A | 6/1980 | Sisson | |
| 4,211,807 A | 7/1980 | Yazawa et al. | |
| 4,239,578 A | 12/1980 | Gore | |
| 4,241,123 A | 12/1980 | Shih | |
| 4,248,652 A | 2/1981 | Civardi et al. | |
| 4,259,220 A | 3/1981 | Bunnelle et al. | 260/27 |
| 4,269,888 A | 5/1981 | Ejima et al. | 428/296 |
| 4,285,998 A | 8/1981 | Thibodeau | |
| 4,300,562 A | 11/1981 | Pieniak | |
| 4,302,495 A | 11/1981 | Marra | |
| 4,303,571 A | 12/1981 | Jansen et al. | |
| 4,304,234 A | 12/1981 | Hartmann | |
| 4,310,594 A | 1/1982 | Yamazaki et al. | |
| 4,319,572 A | 3/1982 | Widlund et al. | |
| 4,323,534 A | 4/1982 | DesMarais | |
| 4,333,782 A | 6/1982 | Pieniak | |
| 4,340,558 A | 7/1982 | Hendrickson | |
| 4,340,563 A | 7/1982 | Appel et al. | 264/518 |
| 4,375,446 A | 3/1983 | Fujii et al. | |
| 4,402,688 A | 9/1983 | Julemont | |
| 4,405,397 A | 9/1983 | Teed | |
| 4,413,623 A | 11/1983 | Pieniak | |
| 4,417,935 A | 11/1983 | Spencer | |
| 4,418,123 A | 11/1983 | Bunnelle et al. | 428/517 |
| 4,438,167 A | 3/1984 | Schwarz | |
| 4,440,819 A | 4/1984 | Rosser et al. | |
| 4,469,540 A | 9/1984 | Furukawa et al. | 156/62.4 |
| 4,490,427 A | 12/1984 | Grant et al. | |
| 4,496,417 A | 1/1985 | Haake et al. | |
| 4,500,316 A | 2/1985 | Damico | |
| 4,507,163 A | 3/1985 | Menard | |
| 4,522,863 A | 6/1985 | Keck et al. | |
| 4,525,407 A | 6/1985 | Ness | |
| 4,543,099 A | 9/1985 | Bunnelle et al. | 604/385 |
| 4,548,859 A | 10/1985 | Kline et al. | |
| 4,552,795 A | 11/1985 | Hansen et al. | |
| 4,555,811 A | 12/1985 | Shimalla | |
| 4,572,752 A | 2/1986 | Jensen et al. | |
| 4,586,199 A | 5/1986 | Birring | |
| D284,036 S | 6/1986 | Birring | |
| 4,606,964 A | 8/1986 | Wideman | 428/152 |
| 4,618,384 A | 10/1986 | Sabee | 156/205 |
| 4,626,305 A | 12/1986 | Suzuki et al. | |
| 4,636,419 A | 1/1987 | Madsen et al. | |
| 4,640,859 A | 2/1987 | Hansen et al. | |
| 4,644,045 A | 2/1987 | Fowells | |
| 4,652,487 A | 3/1987 | Morman | |
| 4,656,081 A | 4/1987 | Ando et al. | |
| 4,657,793 A | 4/1987 | Fisher | |
| 4,657,802 A | 4/1987 | Morman | |
| 4,661,389 A | 4/1987 | Mudge et al. | |
| 4,663,220 A | 5/1987 | Wisneski et al. | |
| 4,666,542 A | 5/1987 | Kawano | |
| 4,675,068 A | 6/1987 | Lundmark | |
| 4,683,877 A | 8/1987 | Ersfeld et al. | |
| 4,687,477 A | 8/1987 | Suzuki et al. | |
| 4,692,368 A | 9/1987 | Taylor et al. | |
| 4,692,371 A | 9/1987 | Morman et al. | |
| 4,696,779 A | 9/1987 | Wideman | 264/211.13 |
| 4,698,242 A | 10/1987 | Salerno | 427/208.2 |
| 4,699,941 A | 10/1987 | Salerno | 524/308 |
| 4,704,116 A | 11/1987 | Enloe | |
| 4,718,901 A | 1/1988 | Singheimer | |
| 4,719,261 A | 1/1988 | Bunnelle et al. | 525/97 |
| 4,720,415 A | 1/1988 | Vander Wielen et al. | 428/152 |
| 4,725,468 A | 2/1988 | McIntyre | |
| 4,726,874 A | 2/1988 | VanVliet | |
| 4,734,311 A | 3/1988 | Sokolowski | |
| 4,734,320 A | 3/1988 | Ohira et al. | |
| 4,734,447 A | 3/1988 | Hattori et al. | |
| 4,735,673 A | 4/1988 | Piron | |
| 4,756,942 A | 7/1988 | Aichele | |
| 4,761,198 A | 8/1988 | Salerno | 156/334 |
| 4,762,582 A | 8/1988 | de Jonckheere | |
| 4,775,579 A | 10/1988 | Hagy et al. | |
| 4,777,080 A | 10/1988 | Harris, Jr. et al. | |
| 4,789,699 A | 12/1988 | Kieffer et al. | |
| 4,798,603 A | 1/1989 | Meyer et al. | |
| 4,801,345 A | 1/1989 | Dussaud et al. | |
| 4,801,482 A | 1/1989 | Goggans et al. | |
| 4,803,117 A | 2/1989 | Daponte | |
| 4,804,577 A | 2/1989 | Hazelton et al. | |
| 4,816,094 A | 3/1989 | Pomplun et al. | 156/85 |
| 4,818,597 A | 4/1989 | DaPonte et al. | |
| 4,826,415 A | 5/1989 | Mende | |
| 4,837,715 A | 6/1989 | Ungpiyakul et al. | |
| 4,842,666 A | 6/1989 | Werenicz | |
| 4,854,985 A | 8/1989 | Soderlund et al. | |
| 4,854,989 A | 8/1989 | Singheimer | |
| 4,863,779 A * | 9/1989 | Daponte | 428/152 |
| 4,867,735 A | 9/1989 | Wogelius | |
| 4,874,447 A | 10/1989 | Hazelton et al. | |
| 4,883,482 A | 11/1989 | Gandrez et al. | |
| 4,883,549 A | 11/1989 | Frost et al. | |
| 4,891,258 A | 1/1990 | Fahrenkrug | |
| 4,892,536 A | 1/1990 | DesMarais et al. | |
| 4,892,903 A | 1/1990 | Himes | |
| 4,900,619 A | 2/1990 | Ostrowski et al. | |
| 4,906,507 A | 3/1990 | Grynaeus et al. | |
| 4,908,247 A | 3/1990 | Baird et al. | |

| | | | | | | |
|---|---|---|---|---|---|---|
| 4,908,253 A | 3/1990 | Rasmussen | | 5,332,613 A | 7/1994 | Taylor et al. |
| 4,910,064 A | 3/1990 | Sabee | | 5,334,437 A | 8/1994 | Zafiroglu |
| 4,917,696 A | 4/1990 | De Jonckheere | | 5,334,446 A | 8/1994 | Quantrille et al. |
| 4,917,746 A | 4/1990 | Kons et al. | | 5,336,545 A | 8/1994 | Morman |
| 4,929,492 A | 5/1990 | Carey, Jr. et al. | | 5,336,552 A | 8/1994 | Strack et al. ............... 428/224 |
| 4,935,021 A | 6/1990 | Huffman et al. | | 5,342,341 A | 8/1994 | Igaue et al. |
| 4,938,757 A | 7/1990 | Van Gompel et al. | | 5,342,469 A | 8/1994 | Bodford et al. |
| 4,938,821 A | 7/1990 | Soderlund et al. | | 5,360,854 A | 11/1994 | Bozich, Jr. |
| 4,940,464 A | 7/1990 | Van Gompel et al. | | 5,364,382 A | 11/1994 | Latimer et al. |
| 4,965,122 A | 10/1990 | Morman ..................... 428/255 | | 5,366,793 A | 11/1994 | Fitts, Jr. et al. ............. 428/198 |
| 4,968,313 A | * 11/1990 | Sabee ..................... 604/385.3 | | 5,376,198 A | 12/1994 | Fahrenkrug et al. |
| 4,970,259 A | 11/1990 | Mitchell et al. | | 5,376,430 A | 12/1994 | Swenson et al. |
| 4,977,011 A | 12/1990 | Smith | | 5,382,400 A | 1/1995 | Pike et al. .................. 264/168 |
| 4,984,584 A | 1/1991 | Hansen et al. | | 5,385,775 A | 1/1995 | Wright ....................... 428/284 |
| 4,994,508 A | 2/1991 | Shiraki et al. | | 5,389,168 A | 2/1995 | Litchholt et al. ............. 156/77 |
| 4,995,928 A | 2/1991 | Sabee | | 5,389,173 A | 2/1995 | Merkatoris et al. |
| 4,998,929 A | 3/1991 | Bjorksund et al. | | 5,393,599 A | 2/1995 | Quantrille et al. |
| 5,000,806 A | 3/1991 | Merkatoris et al. | | 5,399,219 A | 3/1995 | Roessler et al. |
| 5,002,815 A | 3/1991 | Yamanaka et al. | | 5,405,682 A | 4/1995 | Shawyer et al. |
| 5,005,215 A | 4/1991 | McIlquham | | 5,407,507 A | 4/1995 | Ball |
| 5,013,785 A | 5/1991 | Mizui | | 5,411,618 A | 5/1995 | Jocewicz, Jr. |
| 5,028,646 A | 7/1991 | Miller et al. | | 5,413,654 A | 5/1995 | Igaue et al. |
| 5,034,008 A | 7/1991 | Breitkopf | | 5,413,849 A | 5/1995 | Austin et al. |
| 5,045,133 A | 9/1991 | DaPonte et al. | | 5,415,644 A | 5/1995 | Enloe |
| 5,046,272 A | 9/1991 | Vogt et al. | | 5,415,649 A | 5/1995 | Watanabe et al. |
| 5,060,349 A | 10/1991 | Walton et al. | | 5,415,925 A | 5/1995 | Austin et al. |
| 5,073,436 A | 12/1991 | Antonacci et al. | | 5,422,172 A | 6/1995 | Wu |
| 5,093,422 A | 3/1992 | Himes | | 5,425,987 A | 6/1995 | Shawver et al. |
| 5,100,435 A | 3/1992 | Onwumere | | 5,429,629 A | 7/1995 | Latimer et al. |
| 5,104,116 A | 4/1992 | Pohjola | | 5,429,694 A | 7/1995 | Herrmann |
| 5,108,820 A | 4/1992 | Kaneko et al. ............. 428/198 | | 5,431,644 A | 7/1995 | Sipinen et al. |
| 5,112,889 A | 5/1992 | Miller et al. | | 5,431,991 A | 7/1995 | Quantrille et al. |
| 5,114,087 A | 5/1992 | Fisher et al. | | 5,447,462 A | 9/1995 | Smith et al. |
| 5,116,662 A | 5/1992 | Morman | | 5,447,508 A | 9/1995 | Numano et al. |
| 5,147,487 A | 9/1992 | Nomura et al. | | 5,449,353 A | 9/1995 | Watanabe et al. |
| 5,163,932 A | 11/1992 | Nomura et al. | | 5,462,793 A | 10/1995 | Isoda et al. .................. 428/297 |
| D331,627 S | 12/1992 | Igaue et al. | | 5,464,401 A | 11/1995 | Hasse et al. |
| 5,169,706 A | 12/1992 | Collier, IV et al. | | 5,472,775 A | 12/1995 | Obijeski et al. |
| 5,169,712 A | 12/1992 | Tapp | | 5,476,458 A | 12/1995 | Glaug et al. |
| 5,171,633 A | 12/1992 | Muramoto et al. ......... 428/376 | | 5,476,563 A | 12/1995 | Nakata |
| 5,176,668 A | 1/1993 | Bernardin | | 5,484,645 A | 1/1996 | Lickfield et al. |
| 5,176,672 A | 1/1993 | Bruemmer et al. | | 5,486,166 A | 1/1996 | Bishop et al. |
| 5,186,779 A | 2/1993 | Tubbs | | 5,490,846 A | 2/1996 | Ellis et al. |
| 5,192,606 A | 3/1993 | Proxmire et al. | | 5,496,298 A | 3/1996 | Kuepper et al. |
| 5,198,281 A | 3/1993 | Muzzy et al. | | 5,498,468 A | 3/1996 | Blaney |
| 5,200,246 A | 4/1993 | Sabee | | 5,500,075 A | 3/1996 | Herrmann |
| 5,204,429 A | 4/1993 | Kaminsky et al. | | 5,501,679 A | 3/1996 | Krueger et al. |
| D335,707 S | 5/1993 | Igaue et al. | | 5,503,919 A | 4/1996 | Litchholt et al. ............ 428/286 |
| 5,209,801 A | 5/1993 | Smith | | 5,509,915 A | 4/1996 | Hanson et al. |
| 5,219,633 A | 6/1993 | Sabee ......................... 428/109 | | 5,514,470 A | 5/1996 | Haffner et al. |
| 5,224,405 A | 7/1993 | Pohjola | | 5,516,476 A | 5/1996 | Haggard et al. |
| 5,226,992 A | 7/1993 | Morman | | 5,523,146 A | 6/1996 | Bodford et al. |
| 5,229,191 A | 7/1993 | Austin | | 5,527,300 A | 6/1996 | Sauer |
| 5,232,777 A | 8/1993 | Sipinen et al. | | 5,531,850 A | 7/1996 | Herrmann |
| 5,236,430 A | 8/1993 | Bridges | | 5,534,330 A | 7/1996 | Groshens |
| 5,236,770 A | 8/1993 | Assent et al. | | 5,536,563 A | 7/1996 | Shah et al. .................. 428/224 |
| 5,238,733 A | 8/1993 | Joseph et al. | | 5,540,796 A | 7/1996 | Fries |
| 5,246,433 A | 9/1993 | Hasse et al. | | 5,540,976 A | 7/1996 | Shawver et al. |
| D340,283 S | 10/1993 | Igaue et al. | | 5,543,206 A | 8/1996 | Austin et al. |
| 5,252,170 A | 10/1993 | Schaupp | | 5,545,158 A | 8/1996 | Jessup |
| 5,259,902 A | 11/1993 | Muckenfuhs | | 5,545,285 A | 8/1996 | Johnson |
| 5,260,126 A | 11/1993 | Collier, IV et al. | | 5,549,964 A | 8/1996 | Shohji et al. |
| 5,272,236 A | 12/1993 | Lai et al. | | 5,569,232 A | 10/1996 | Roe et al. |
| 5,278,272 A | 1/1994 | Lai et al. | | 5,575,783 A | 11/1996 | Clear et al. |
| 5,288,791 A | 2/1994 | Collier, IV et al. | | 5,576,090 A | 11/1996 | Suzuki |
| 5,290,842 A | 3/1994 | Sasaki et al. | | 5,582,668 A | 12/1996 | Kling |
| 5,296,080 A | 3/1994 | Merkatoris et al. | | 5,591,152 A | 1/1997 | Buell et al. |
| 5,304,599 A | 4/1994 | Himes | | 5,591,792 A | 1/1997 | Hattori et al. |
| 5,308,345 A | 5/1994 | Herrin | | 5,593,525 A | 1/1997 | Isoda et al. .................. 156/622 |
| 5,312,500 A | 5/1994 | Kurihara et al. | | 5,593,768 A | 1/1997 | Gessner ....................... 428/286 |
| 5,324,580 A | 6/1994 | Allan et al. | | 5,595,618 A | 1/1997 | Fries et al. |

| Patent No. | Date | Inventor(s) | Class |
|---|---|---|---|
| 5,597,430 A | 1/1997 | Rasche | |
| 5,612,118 A | 3/1997 | Schleinz et al. | |
| 5,614,276 A | 3/1997 | Petsetakis | |
| 5,620,780 A | 4/1997 | Krueger et al. | |
| 5,624,740 A | 4/1997 | Nakata | |
| 5,626,573 A | 5/1997 | Igaue et al. | |
| 5,628,856 A | 5/1997 | Dobrin et al. | |
| 5,645,672 A | 7/1997 | Dobrin | |
| 5,652,041 A | 7/1997 | Buerger et al. | |
| 5,660,664 A | 8/1997 | Herrmann | |
| 5,663,228 A | 9/1997 | Sasaki et al. | |
| 5,669,897 A | 9/1997 | Lavon et al. | |
| 5,674,216 A | 10/1997 | Buell et al. | |
| 5,677,057 A | 10/1997 | Tashiro et al. | 428/376 |
| 5,680,653 A | 10/1997 | Mathis et al. | |
| 5,681,302 A | 10/1997 | Melbye et al. | |
| 5,683,787 A | 11/1997 | Boich et al. | |
| 5,690,626 A | 11/1997 | Suzuki et al. | |
| 5,691,034 A | 11/1997 | Krueger et al. | |
| 5,693,038 A | 12/1997 | Suzuki et al. | |
| 5,695,849 A | 12/1997 | Shawver et al. | |
| 5,702,378 A | 12/1997 | Widlund et al. | |
| 5,707,709 A | 1/1998 | Blake | |
| 5,709,921 A | 1/1998 | Shawver | |
| 5,720,838 A | 2/1998 | Nakata | |
| 5,733,635 A | 3/1998 | Terakawa et al. | |
| 5,733,822 A * | 3/1998 | Gessner et al. | 442/35 |
| 5,735,839 A | 4/1998 | Kawaguchi et al. | |
| 5,736,219 A | 4/1998 | Suehr et al. | |
| 5,746,731 A | 5/1998 | Hisada | |
| 5,749,865 A | 5/1998 | Yamamoto et al. | |
| 5,749,866 A | 5/1998 | Roe et al. | |
| 5,766,389 A | 6/1998 | Brandon et al. | |
| 5,766,737 A | 6/1998 | Willey et al. | |
| 5,769,838 A | 6/1998 | Buell et al. | |
| 5,769,993 A | 6/1998 | Baldauf | |
| 5,772,649 A | 6/1998 | Siudzinski | |
| 5,773,373 A | 6/1998 | Wynne et al. | |
| 5,773,374 A | 6/1998 | Wood et al. | |
| 5,780,155 A | 7/1998 | Ishizawa et al. | 428/370 |
| 5,788,804 A | 8/1998 | Horsting | |
| 5,789,065 A | 8/1998 | Haffner et al. | |
| 5,789,328 A | 8/1998 | Kurihara et al. | |
| 5,789,474 A | 8/1998 | Lu et al. | |
| 5,800,903 A | 9/1998 | Wood et al. | |
| 5,804,021 A | 9/1998 | Abuto et al. | |
| 5,804,286 A * | 9/1998 | Quantrille et al. | 428/198 |
| 5,814,176 A | 9/1998 | Proulx | |
| 5,817,087 A | 10/1998 | Takabayashi et al. | |
| 5,818,719 A | 10/1998 | Brandon et al. | |
| 5,830,203 A | 11/1998 | Suzuki et al. | |
| 5,834,089 A | 11/1998 | Jones et al. | |
| 5,836,931 A | 11/1998 | Toyoda et al. | |
| 5,836,932 A | 11/1998 | Buell et al. | |
| 5,840,412 A | 11/1998 | Wood et al. | |
| 5,840,633 A | 11/1998 | Kurihara et al. | |
| 5,846,232 A | 12/1998 | Serbiak et al. | |
| 5,849,001 A | 12/1998 | Torimae et al. | |
| 5,856,387 A | 1/1999 | Sasaki et al. | |
| 5,858,528 A | 1/1999 | Tashiro et al. | 428/357 |
| 5,860,945 A | 1/1999 | Cramer et al. | |
| 5,865,933 A | 2/1999 | Morin et al. | |
| 5,876,392 A | 3/1999 | Hisada | |
| 5,879,776 A | 3/1999 | Nakata | |
| 5,882,573 A | 3/1999 | Kwok et al. | |
| 5,883,028 A * | 3/1999 | Morman et al. | 442/394 |
| 5,885,656 A | 3/1999 | Goldwasser | |
| 5,885,686 A | 3/1999 | Cederblad et al. | |
| 5,895,382 A | 4/1999 | Popp et al. | 604/385.21 |
| 5,897,546 A | 4/1999 | Kido et al. | |
| 5,899,895 A | 5/1999 | Robles et al. | |
| 5,902,540 A | 5/1999 | Kwok | |
| 5,904,298 A | 5/1999 | Kwok et al. | |
| 5,906,879 A | 5/1999 | Huntoon et al. | 428/136 |
| 5,916,206 A | 6/1999 | Otsubo et al. | |
| 5,921,973 A | 7/1999 | Newkirk et al. | |
| 5,930,139 A | 7/1999 | Chapdelaine et al. | |
| 5,931,581 A | 8/1999 | Garberg et al. | |
| 5,932,039 A | 8/1999 | Popp et al. | |
| 5,941,865 A | 8/1999 | Otsubo et al. | |
| D414,262 S | 9/1999 | Ashton et al. | |
| 5,952,252 A * | 9/1999 | Shawver et al. | 442/407 |
| 5,964,970 A | 10/1999 | Woolwine et al. | |
| 5,964,973 A | 10/1999 | Heath et al. | |
| 5,990,377 A | 11/1999 | Chen et al. | |
| 5,993,433 A | 11/1999 | St. Louis et al. | |
| 5,993,944 A | 11/1999 | Honna et al. | 428/198 |
| 5,997,521 A | 12/1999 | Robles et al. | |
| 6,001,752 A | 12/1999 | Ishizawa et al. | 442/632 |
| 6,004,306 A | 12/1999 | Robles et al. | |
| 6,009,558 A | 1/2000 | Rosch et al. | |
| 6,033,502 A | 3/2000 | Coenen et al. | |
| 6,045,543 A | 4/2000 | Pozniak et al. | |
| 6,048,326 A | 4/2000 | Davis et al. | |
| 6,057,024 A | 5/2000 | Mleziva et al. | 428/114 |
| 6,066,369 A | 5/2000 | Schulz et al. | |
| 6,087,550 A | 7/2000 | Anderson-Fischer et al. | |
| 6,090,234 A | 7/2000 | Barone et al. | |
| 6,092,002 A | 7/2000 | Kastman et al. | |
| 6,093,663 A | 7/2000 | Ouellette et al. | |
| 6,096,668 A | 8/2000 | Abuto et al. | |
| 6,123,694 A | 9/2000 | Pieniak et al. | |
| 6,132,410 A | 10/2000 | Van Gompel et al. | |
| 6,152,904 A | 11/2000 | Matthews et al. | |
| 6,169,848 B1 | 1/2001 | Henry | |
| 6,183,587 B1 | 2/2001 | McFall et al. | |
| 6,183,847 B1 | 2/2001 | Goldwasser | |
| 6,197,012 B1 | 3/2001 | Mishima et al. | 604/385.04 |
| 6,214,476 B1 | 4/2001 | Ikeda et al. | |
| 6,217,690 B1 | 4/2001 | Rajala et al. | |
| 6,221,483 B1 | 4/2001 | Hilston et al. | 428/343 |
| 6,231,557 B1 | 5/2001 | Krautkramer et al. | |
| 6,238,379 B1 | 5/2001 | Keuhn, Jr. et al. | |
| 6,245,050 B1 | 6/2001 | Odorzynski et al. | |
| 6,245,168 B1 | 6/2001 | Coenen et al. | |
| 6,260,211 B1 | 7/2001 | Rajala et al. | |
| 6,279,807 B1 | 8/2001 | Crowley et al. | |
| 6,290,979 B1 | 9/2001 | Roe et al. | |
| 6,310,164 B1 | 10/2001 | Morizono et al. | |
| 6,316,013 B1 | 11/2001 | Paul et al. | |
| 6,316,687 B1 | 11/2001 | Davis et al. | |
| 6,316,688 B1 | 11/2001 | Hammons et al. | |
| 6,320,096 B1 | 11/2001 | Inoue et al. | |
| 6,323,389 B1 | 11/2001 | Thomas et al. | |
| 6,329,459 B1 | 12/2001 | Kang et al. | |
| 6,364,863 B1 | 4/2002 | Yamamoto et al. | |
| 6,365,659 B1 | 4/2002 | Aoyama et al. | |
| 6,417,121 B1 * | 7/2002 | Newkirk et al. | 442/364 |
| 6,475,600 B1 * | 11/2002 | Morman et al. | 428/152 |
| 6,537,935 B1 | 3/2003 | Seth et al. | |
| 6,562,167 B2 | 5/2003 | Coenen et al. | 156/73.1 |
| 2002/0002021 A1 | 1/2002 | May et al. | |
| 2002/0009940 A1 | 1/2002 | May et al. | |
| 2002/0019616 A1 | 2/2002 | Thomas | |
| 2002/0104608 A1 | 8/2002 | Welch et al. | |
| 2002/0138063 A1 | 9/2002 | Kuen et al. | |
| 2002/0164465 A1 | 11/2002 | Curro et al. | |

FOREIGN PATENT DOCUMENTS

| | | | |
|---|---|---|---|
| EP | 0 617 939 | 10/1994 | A61F/13/15 |
| EP | 0 688 550 | 12/1995 | A61F/13/15 |
| EP | 0 689 815 | 1/1996 | A61F/13/15 |

| | | | | | | | | |
|---|---|---|---|---|---|---|---|---|
| EP | 0 713 546 | 5/1996 | ........... D04H/13/00 | WO | WO 95/04182 | 2/1995 | ........... D04H/13/00 |
| EP | 0 743 052 | 11/1996 | ........... A61F/13/15 | WO | WO 95/16425 | 6/1995 | ........... A61F/13/58 |
| EP | 0 747 521 A2 | 12/1996 | | WO | WO 95/16562 | 6/1995 | ............ B32B/5/24 |
| EP | 0 753 292 | 1/1997 | ........... A61F/13/15 | WO | WO 95/22644 | 8/1995 | |
| EP | 0 761 193 | 3/1997 | ........... A61F/13/15 | WO | WO 95/34264 | 12/1995 | ........... A61F/13/15 |
| EP | 0 761 194 | 3/1997 | ........... A61F/13/15 | WO | WO 96/13989 | 5/1996 | ............ A41B/9/00 |
| EP | 0 763 353 | 3/1997 | ........... A61F/13/15 | WO | WO 96/23466 | 8/1996 | ........... A61F/13/15 |
| EP | 0 787 474 | 8/1997 | ........... A61F/13/15 | WO | WO 96/35402 | 11/1996 | ........... A61F/13/15 |
| EP | 0 806 196 | 11/1997 | ........... A61F/13/15 | WO | WO 97/17046 | 5/1997 | ........... A61F/13/15 |
| EP | 0 814 189 | 12/1997 | ......... D04H/13/00 | WO | WO 98/14156 | 4/1998 | ........... A61F/13/15 |
| EP | 0 873 738 | 10/1998 | ........... A61F/13/15 | WO | WO 98/49988 | 11/1998 | ........... A61F/13/15 |
| EP | 0 888 101 | 1/1999 | ........... A61F/13/15 | WO | WO 98/55062 | 12/1998 | ........... A61F/13/15 |
| EP | 0 901 780 | 3/1999 | ........... A61F/13/15 | WO | WO 99/17926 | 4/1999 | ............ B32B/5/04 |
| EP | 1 013 251 | 6/2000 | ........... A61F/13/15 | WO | WO 99/24519 | 5/1999 | .............. C09J/7/02 |
| EP | WO0037723 * | 8/2000 | | WO | WO 99/47590 | 9/1999 | .............. C08J/5/18 |
| GB | 2 244 422 | 12/1991 | ........... A61F/13/15 | WO | WO 99/60969 | 12/1999 | ........... A61F/13/15 |
| GB | 2 250 921 | 6/1992 | ........... A61F/13/15 | WO | WO 99/60970 | 12/1999 | ........... A61F/13/15 |
| GB | 2 253 131 | 9/1992 | ........... A61F/13/72 | WO | WO 99/60971 | 12/1999 | ........... A61F/13/15 |
| GB | 2 267 024 | 11/1993 | ........... A61F/13/66 | WO | WO 00/10500 | 3/2000 | ........... A61F/13/15 |
| GB | 2 266 389 | 1/1994 | ........... A61F/13/15 | WO | WO 00/28123 | 5/2000 | |
| IS | 92891 | 2/1992 | | WO | WO 00/29199 | 5/2000 | ........... B29C/55/18 |
| JP | 61194221 A | 8/1986 | | WO | WO 00/29655 | 5/2000 | |
| JP | 3000814 A | 1/1991 | | WO | WO 00/29657 | 5/2000 | |
| JP | 03-067646 | 3/1991 | ............. B32B/5/28 | WO | WO 00/37003 | 6/2000 | ........... A61F/13/15 |
| JP | 3069614 A | 3/1991 | | WO | WO 00/37005 | 6/2000 | ........... A61F/13/15 |
| JP | 3161330 A | 7/1991 | | WO | WO 00/37723 | 6/2000 | |
| JP | 6306708 A | 11/1994 | | WO | WO 00/59429 | 10/2000 | ........... A61F/13/15 |
| JP | 2000154428 A | 6/2000 | | WO | WO 01/00053 | 1/2001 | ........... A61F/13/15 |
| WO | WO 90/03464 | 4/1990 | ............ D04H/1/56 | WO | WO 01/32116 | 5/2001 | ........... A61L/15/22 |
| WO | WO 91/07277 | 5/1991 | ............. B32B/5/04 | WO | WO 01/49907 A2 | 7/2001 | |
| WO | WO 92/16371 | 10/1992 | ............ B32B/31/00 | WO | WO 01/87214 | 11/2001 | ......... A61F/13/496 |
| WO | WO 93/15247 | 8/1993 | ............ D04H/1/48 | WO | WO 02/34184 | 5/2002 | ............ A61F/13/49 |
| WO | WO 93/15249 | 8/1993 | | WO | WO 02/060690 | 8/2002 | ............ B32B/27/32 |
| WO | WO 93/17648 | 9/1993 | ........... A61F/13/15 | | | | |
| WO | WO 94/09736 | 5/1994 | ........... A61F/13/15 | | | | |
| WO | WO 95/03443 | 2/1995 | .......... D04H/13/00 | * cited by examiner | | | |

ELASTIC STRAND BONDED LAMINATE

BACKGROUND

In the field of elastic laminate garment panels for disposable or limited use garments, desirable qualities include light weight, good skin feel (hand) and exterior abrasion resistance, good flexibility and bond strength. Generally such elastic laminates may be made with a first facing of good hand to contact the skin of the wearer in a non-irritating manner. A second, exterior, facing is used for the exterior side of the garment facing away from the skin of the wearer. Between the two facings is applied an adhesive and strands or webs of elastic material.

However a first problem occurs with such elastic laminates in getting the facings to adhere to each other, and the tensioned elastics, without debonding. This can especially be problematic when the garment is wet, e.g. in swim pants which are subject to total immersion. A second problem occurs aesthetically when, as more adhesive is added to construct the laminate, the heavier, and stiffer, or less flexible, the material becomes. Standard methodology generally requires spraying an entire layer of adhesive down, which leads to a loss of aesthetic cloth-like qualities. Also, as more steps or materials are put into making a fabric (such as adhesive spraying) the more equipment and material is required, leading to a loss of economy.

Hot melt applied adhesives may require the use of adhesives applied in a liquid state and may have problems including increased energy consumption, increased thickness, process control and change time, in addition to the above-stated problems. Meltbonding of the facings may require that the facing webs or the elastic strands or webs, or both, of thermoplastic material be brought at least partially to their melting point in order to bond. These meltbonding techniques may share the same heat-associated problems as hot melt applications and may further suffer cosmetic and lamination strength problems as well as loss of cloth like feel.

Thus there is need to provide economical, light weight, easily manufactured nonwoven laminates having desirable aesthetic qualities.

SUMMARY

The present invention solves the above-stated needs in the art by providing a simplified elastomeric laminate made, in one aspect of the invention, from nonwoven facings and thermoplastic adhesive elastomeric fiber strands. A plurality of thermoplastic adhesive elastomeric fiber strands are located between first and second facing webs. The fibers have an elastic core and adhesive-enriched surfaces. Thus the core is free to perform its primary elastic function while the sheath or surface is free to perform the primary adhesive function without undue corruption of the primary functions resulting from an attempt to derive both functions from a single composition. The facing webs, with the elastomeric fiber strands between them, are calendered together, thus adhering the facing webs together via contact adhesion with the elastomeric fibers. Thus no extra material, machinery, or steps for separate placement of adhesives is required.

Without excessive adhesive, the laminates are lighter, and more flexible while still retaining excellent bond strength between the layers and desired aesthetics. Further, because the strand construction may allow the facings to remain free between the strands, additional bulk and softness may be obtained with the present invention while still providing adequate strand-to-facing and facing-to-facing adhesion. Heretofore, no one is believed to have taught such an elastic laminate using tacky, or adhesive, elastomeric strands, because the person having ordinary skill in the art would likely consider such adhesive strands to be too difficult to work with in a practical manufacturing setting.

Elastic adhesive fibers suitable for use with the present invention may be spunbond (SB) bicomponent or meltblown (MB) bicomponent fibers with a tacky sheath, or may be homofilament fibers loaded with an adhesive which will aggregate or concentrate at, or migrate to, the surface of the fibers. The process may be a vertical filament laminate (VFL) process, such as for making vertical filament stretch-bonded laminate (VFSBL) material, as disclosed in copending application WO 01/87588 published Nov. 22, 2001 and entitled Targeted Elastic Laminate, or a horizontal/continuous filament laminate (CFL) manufacturing process, such as for making continuous filament stretch-bonded laminate (CFSBL) material, as disclosed in U.S. Pat. No. 5,385,775 issued Jan. 31, 1995 to Wright; all of which are incorporated by reference herein in their entirety.

The facings may be nonwoven laminates such as, without limitation, about a 0.1 osy to about a 4.0 osy nonwoven, with a particular example being a 0.4 osy polypropylene spunbond nonwoven web and may be gatherable or expandable, or both in the desired direction, or axis, of elasticity for the laminate in order to provide for expansion and contraction of the resulting laminate.

DEFINITIONS

The term "bicomponent filaments" or "bicomponent fibers" refers to fibers which have been formed from at least two polymers extruded and formed together to create one fiber and may also be referred to herein as "conjugate" or "multicomponent" fibers. "Bicomponent" is not meant to be limiting to only two constituent polymers unless otherwise specifically indicated. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, or a side-by-side-by-side, arrangement. Bicomponent fibers are generally taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. Conventional additives, such as pigments and surfactants, may be incorporated into one or both polymer streams, or applied to the filament surfaces.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates, and materials added to enhance processability of the composition.

The term "contact adhesion" or "contact adherence" refers to an adhesive system whereby a tacky surface adheres to create a bond without the necessity of one of the materials entering a liquid state to create the bond.

"Homofilament" refers to a fiber formed from only one predominate polymer and made from a single stream of that polymer. This is not meant to exclude fibers formed from one polymer to which small amounts of additives have been added for coloration, adhesive properties, anti-static properties, lubrication, hydrophilicity, processability, etc.

As used herein, the term "machine direction" or MD means the length of a fabric in the direction in which it is produced. The term "cross machine direction" or CD means the width of fabric, i.e. a direction generally perpendicular to the MD.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "microfibers" means small diameter fibers having an average diameter not greater than about 75 microns, for example, having an average diameter of from about 1 micron to about 50 microns, or more particularly, having an average diameter of from about 1 micron to about 30 microns. Another frequently used expression of fiber diameter is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc (an assumed polypropylene density for this example) and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

As used herein, the term "neck" or "neck stretch" interchangeably means that the fabric is drawn such that it is extended under conditions reducing its width or its transverse dimension by drawing and elongating to increase the length of the fabric. The controlled drawing may take place under cool temperatures, room temperature or greater temperatures and is limited to an increase in overall dimension in the direction being drawn up to the elongation required to break the fabric. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 issued Oct. 23, 1990 to Morman, which, discloses a process for providing a reversibly necked nonwoven material which may include necking the material, then heating the necked material, followed by cooling.

As used herein, the term "neckable material or layer" means any material which can be necked such as a nonwoven, woven, or knitted material. As used herein, the term "necked material" refers to any material which has been drawn in at least one dimension, (e.g. lengthwise), reducing the transverse dimension, (e.g. width), such that when the drawing force is removed, the material can be pulled back, or relaxed, to its original width. The necked material typically has a higher basis weight per unit area than the un-necked material. When the necked material returns to its original un-necked width, it should have about the same basis weight as the un-necked material. This differs from stretching a material layer, during which the layer is thinned and the basis weight is permanently reduced.

Typically, such necked nonwoven fabric materials are capable of being necked up to about 80 percent. For example, the neckable backsheet 30 of the various aspects of the present invention may be provided by a material that has been necked from about 10 to about 80 percent, desirably from about 20 to about 60 percent, and more desirably from about 30 to about 50 percent for improved performance. For the purposes of the present disclosure, the term "percent necked" or "percent neckdown" refers to a ratio or percentage determined by measuring the difference between the pre-necked dimension and the necked dimension of a neckable material, and then dividing that difference by the pre-necked dimension of the neckable material and multiplying by 100 for percentage. The percentage of necking (percent neck) can be determined in accordance with the description in the above-mentioned U.S. Pat. No. 4,965,122.

The term "nonwoven fabric" or "nonwoven web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air-laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

"Personal care product" or "personal care absorbent article" means diapers, wipes, training pants, absorbent underpants, adult incontinence products, feminine hygiene products, wound care items like bandages, and other like articles.

The term "polymer" generally includes without limitation homopolymers, copolymers (including, for example, block, graft, random and alternating copolymers), terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "spunbond fibers" refers to small diameter fibers which are formed by extruding molten thermoplastic material as filaments from a plurality of fine capillaries of a spinneret having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky when they are deposited onto a collecting surface. Spunbond fibers are generally continuous and usually have average diameters larger than meltblown fibers, and more particularly, generally between about 10 and 30 microns.

The term "substantially continuous filaments" or "substantially continuous fibers" refers to filaments or fibers prepared by extrusion from a spinneret, including without limitation spunbond and meltblown fibers, which are not cut from their original length prior to being formed into a nonwoven web or fabric. Substantially continuous filaments or fibers may have average lengths ranging from greater than about 15 cm to more than one meter, and up to or greater than the length of the nonwoven web or fabric being formed. The definition of "substantially continuous filaments" (or fibers) includes those filaments or fibers which are not cut prior to being formed into a nonwoven web or fabric, but which are later cut when the nonwoven web or fabric is cut.

The term "staple fibers" means fibers which are natural or cut from a manufactured filament prior to forming into a web, and which have an average length ranging from about 0.1–15 cm, more commonly about 0.2–7 cm.

Words of degree, such as "about", "substantially", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

BRIEF DESCRIPTION OF THE DRAWINGS

The accompanying drawings are presented as an aid to explanation and understanding of various aspects of the present invention only and are not to be taken as limiting the present invention. The drawings are not necessarily to scale, nor should they be taken as photographically accurate depictions of real objects unless otherwise stated.

DETAILED DESCRIPTION

Certain aspects and embodiments of the invention will be described in the context of disposable absorbent articles, and may more particularly be referred to, without limitation and by way of illustration, as a disposable training pant garment or swim wear garment with elastic side panels. It is, however, readily apparent that aspects of the present invention can also be employed to produce other elasticized areas and for other garment or personal care article types, such as feminine care articles, various incontinence garments, medical garments and any other disposable garments, whether absorbent or not, needing an easily manufactured elasticized area. Typically, such disposable garments are intended for limited use and are not intended to be laundered or otherwise cleaned for reuse. A disposable training pant, for example, is discarded after it has become soiled by the wearer.

Figure 1:
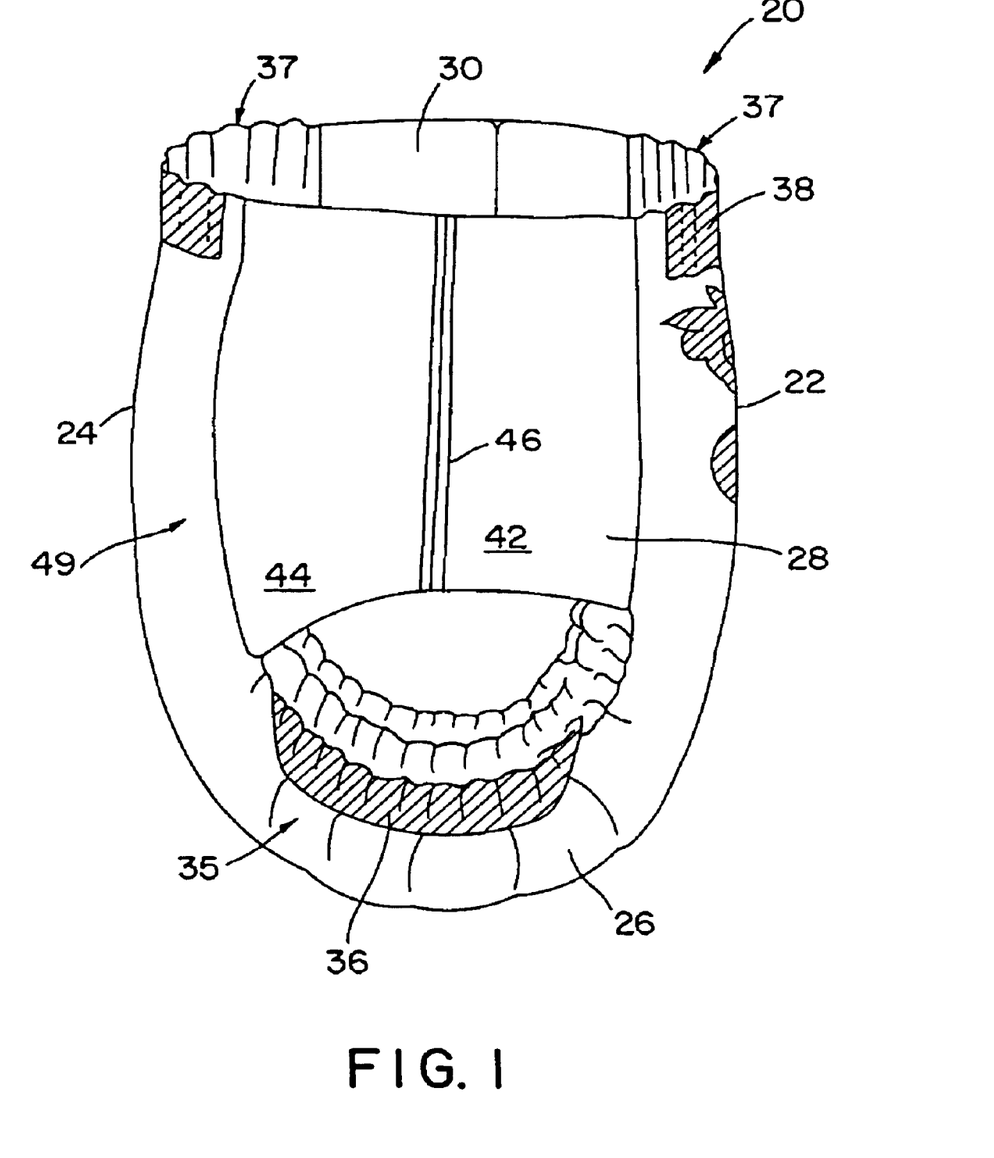
FIG. 1 illustrates a training pant/swim pant which may utilize the elastic laminate of the present invention.

With reference to FIG. 1, the garment 20 generally defines a front waist section 22, a rear waist section 24, and a crotch 26 which interconnects the front and rear waist sections. The front and rear waist sections 22 and 24 include the general portions of the garment which are constructed to extend over the wearer's front and rear abdominal regions, respectively, during use. Elasticized side panels 28, 30, as further explained below, connect the front and rear waist sections 22, 24, respectively. The crotch 26 of the garment includes the general portion of the garment that is constructed to extend through the wearer's crotch region between the legs.

To provide improved fit and to help reduce leakage of body exudates from the garment 20, the garment leg cuffs 35 and waist margins 37 may be elasticized with suitable elastic members. For example, as illustrated in FIG. 1, the garment 20 may include leg elastics 36 which are constructed to operably tension the side margins of the garment 20 to provide elasticized leg bands which can closely fit around the legs of the wearer to reduce leakage and provide improved comfort and appearance. Waist elastics 38 may be employed to elasticize the waist margins 37 of the garment 20 to provide elasticity to the waistband. The waist elastics 38 are configured to help provide a resilient, comfortably close fit around the waist of the wearer.

Referencing FIG. 1, the side panels 28, 30 are also elasticized to provide improved fit and conformance to the wearer. Each side panel, e.g., side panel 28, is composed of a first portion 42, and a second portion 44. The first portion 42 is bonded to the front waist section 22 by any known means such as ultrasonic bonding, adhesives, etc. Likewise the second portion 44 is bonded to the back waist section 24 in similar matter. The free ends of the side panel portions not bonded to the waist sections are then bonded in a standing butt seam 46 to create a side panel area 49. As used herein, the term "standing butt seam" refers to a seam wherein two separate pieces of substrate are bonded together face-to-face or back-to-back in close proximity to an outer edge of each of the pieces of substrate, and the outer edges of the pieces of substrate project outward from the finished product, placing the seam in peel, as opposed to shearing strain. The seam 46 may be substantially permanent or easily separable depending on the garment application.

Figure 2:
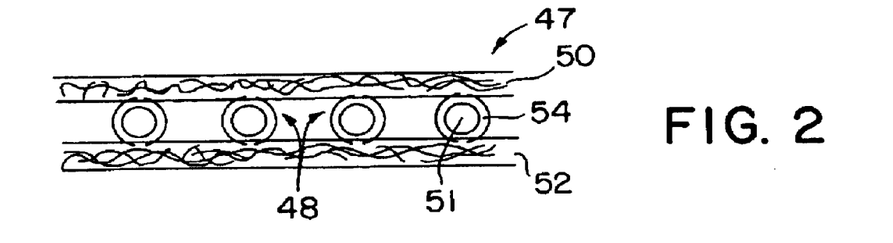
FIGS. 2–4 illustrate transverse, or cross direction, cross sections of alternative embodiments of the elastic adhesive fibers with facings.

Referencing FIG. 2, an exemplary material, or laminate, 47 for the side panel portions is made elastic, flexible, and light weight by placing thermoplastic elastomeric adhesive fibers 48 between a first nonwoven facing 50 and a second nonwoven facing 52 such as 0.4 osy spunbond nonwoven webs. The fibers have elastic cores 51 and adhesive-rich sheaths, or outer perimeters 54, which are adhered to the facings, or extendible webs, 50, 52 by contact adhesion. It will of course be appreciated that facing materials may be webs of material other than nonwovens if appropriate. The fibers may be, for example, bicomponent fibers having a core of an elastic polymer blend available from KRATON Polymers of Houston, Tex. containing 70% by weight KRATON® G1730 tetrablock copolymer elastomer and 30% by weight polyethylene wax; and a sheath of KRATON® G2760 polymer which contains a tackifying resin. Such a composition may be suitable for fibers formed on a wire or screen such as in the continuous filament laminate (CFL) process as further explained below. Higher levels of tackifier in the sheath may be obtained with the vertical filament laminate (VFL) process, further explained below wherein the fibers are formed on a chill roll with a release layer coating.

Figure 3:
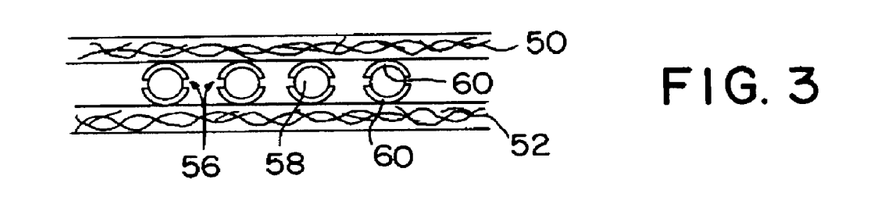

Alternatively, referencing FIG. 3, a bicomponent meltblown fiber of sheath/core (not shown) (especially good for VFL processes), or a partial sheath/core morphology fiber 56 (especially good for CFL processes) with an elastic core polymer 58 and incomplete or partially surrounding, tackifier, or adhesive, rich, outer areas 60, which do not necessarily provide a 360 degree coverage of the core, may be utilized to bond the facings 50, 52 through contact adhesion. The sheaths or surface areas 60 may also be a blend of elastomer and tackifier components.

Figure 4:
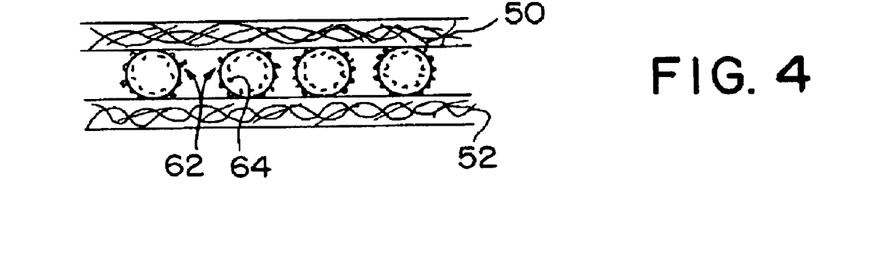

As another alternative, referencing FIG. 4, a homofilament fiber 62, such as polyethylene substantially continuous spunbond fiber is loaded with a selective tackifier 64 which migrates to the surface of the fiber 62. This homofilament fiber with selectively migrating tackifier may thus eliminate any special requirements of bicomponent processing. Examples of such a filament and selective migrating tackifier might include polyethylene fibers with a hydrogenated hydrocarbon resin tackifier.

Figure 5:
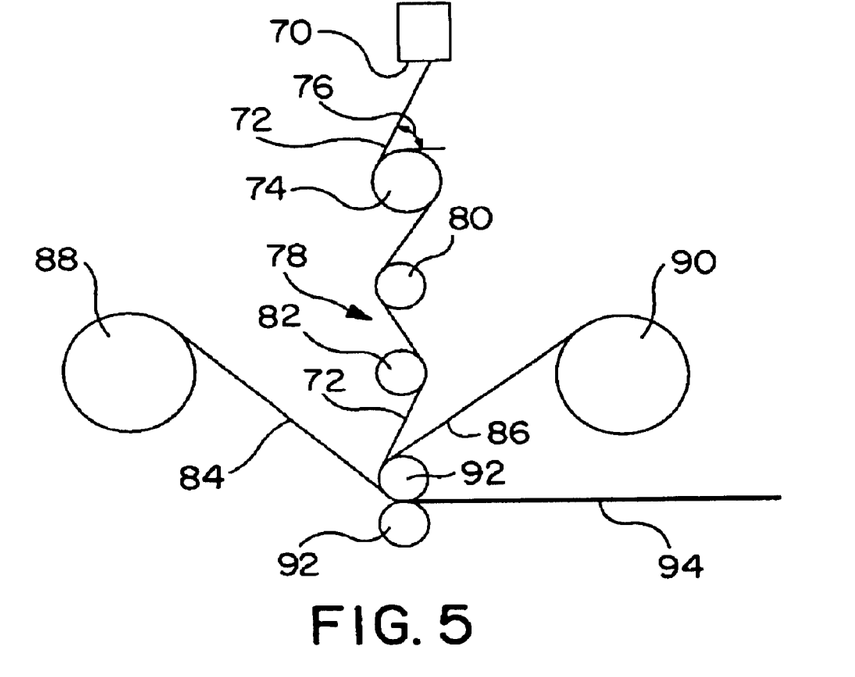
FIG. 5 illustrates a first process for making an elastic laminate of the present invention.

FIG. 5 schematically illustrates a vertical filament laminate (VFL) process for the manufacture of elastic laminates as previously mentioned above. Referring to FIG. 5, at least one molten elastomeric material is extruded from a die extruder 70 through spinning holes as a plurality of substantially continuous elastomeric, adhesive-rich filaments 72. The filaments 72 are quenched and solidified by passing the filaments 72 over a first chill roll 74. Any number of chill rolls can be used. Suitably, chill rolls may have a temperature of about 40 degrees F. to about 80 degrees F. The chill roll 74 may also suitably have a release layer covering (not shown) on the surface to provide for easy release of the adhesive rich filaments, or fibers, 72 which may allow for a higher level of tackifier in the filaments than possible with current horizontal wire processes, as explained in conjunction with FIG. 6.

The die of the extruder 70 may be positioned with respect to the first roller so that the continuous filaments meet this first roller 74 at a predetermined angle 76. This strand extrusion geometry is particularly advantageous for depositing a melt extrudate onto a rotating roll or drum. An angled, or canted, orientation provides an opportunity for the filaments to emerge from the die at a right angle to the roll tangent point resulting in improved spinning, more efficient energy transfer, and generally longer die life. This configuration allows the filaments to emerge at an angle from the die and follow a relatively straight path to contact the tangent point on the roll surface. The angle 76 between the die exit of the extruder 70 and the vertical axis (or the horizontal axis of the first roller, depending on which angle is measured) may be as little as a few degrees or as much as 90 degrees. For example, a 90 degree extrudate exit to roller angle could be achieved by positioning the extruder 70 directly above the downstream edge of the first roller 74 and having a side exit die tip on the extruder. Moreover, angles such as about 20 degrees, about 35 degrees, or about 45 degrees, away from vertical may be utilized. It has been found that, when utilizing a 12-filament/inch spinplate hole density, an approximately 45 degree angle (shown in FIG. 5) allows the system to operate effectively. The optimum angle, however, may vary as a function of extrudate exit velocity, roller speed, vertical distance from the die to the roller, and horizontal distance from the die centerline to the top dead center of the roller. Optimal performance can be achieved by employing various geometries to result in improved spinning efficiency and reduced filament breakage.

After the filaments 72 are quenched and solidified they are stretched or elongated using a first series of stretch rolls 78. The first series of stretch rolls 78 may comprise one or more individual stretch rolls and suitably at least two stretch rolls 80 and 82, as shown in FIG. 5. Stretch rolls 80, 82 rotate at a speed greater than a speed at which chill roll 74 rotates, thereby stretching the filaments 72.

In one embodiment of this invention, each successive roll rotates at a speed greater than the speed of the previous roll. For example, referring to FIG. 5, if the chill roll 74 rotates at a speed "x"; stretch roll 80 rotates at a still greater speed, for example about 1.15×; second stretch roll 82 rotates at a still greater speed, for example about 1.25× to about 7×. As a result, the filaments 72 may be stretched by about 100% to about 800% of an initial pre-stretched length.

After the filaments 72 are stretched, they are laminated to the first facing material 84 and desirably at the same time to a second facing material 86. The first facing material 84 is unwound from a roller 88 and laminated to a first side of the filaments 72. The second facing material 86 is unwound from a second roller 90 and laminated to a second side of the filaments 72. Before the facing materials 84, 86 are laminated to the filaments they may be necked by additional rollers (not shown). The laminate material is then passed through nip rolls 92 to bond the adhesive-surfaced elastic filaments to the facings 84, 86 by contact adhesion. The nip rolls 92, may alternatively be used in place of, or in addition to, the stretch rolls 80, 82 to achieve stretching. The laminate material is then allowed to relax thereby allowing the retracting elastomers to form gathers in the material (see FIG. 8).

The nip rollers may be designed to provide a maximum bond area through the use of flat calender rolls in certain aspects of the invention. Alternatively, a patterned roller may yield certain benefits such as increased bulk or stretching of the laminate and may be used where the strength of the contact adhesion between and among the facings and the strands is not unduly effected. The calender rolls can be heated to a degree below the melting points of the various laminate components, or may be ambient, or chilled.

Figure 6:
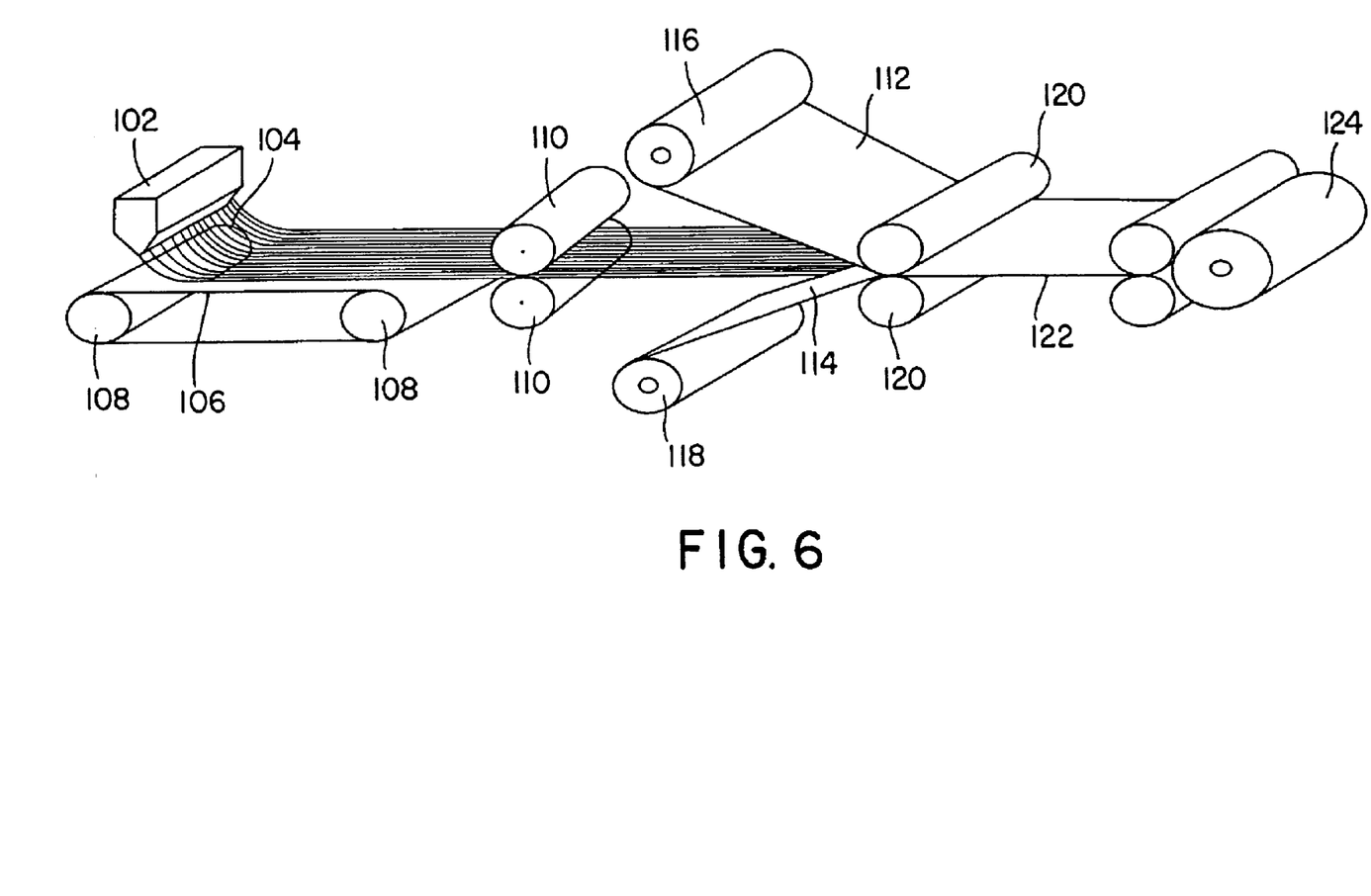
FIG. 6 illustrates a second process for making an elastic laminate of the present invention.

FIG. 6 illustrates a horizontal, continuous filament laminate (CFL) process for making another elastic laminate of the invention. A first extrusion apparatus 102 is fed with an elastomeric polymer or polymer blend from one or more sources (not shown) and provided with the necessary adhesive sheath or selectively migrating adhesive. In various embodiments, the extrusion apparatus 102 can be configured to produce meltblown or spunbond, and bicomponent or homofilament fibers. Techniques for fiber extrusion, such as modified meltblowing of the fibers, are further set forth in the previously mentioned U.S. Pat. No. 5,385,775 to Wright. Apparatus 102 extrudes filaments 104 directly onto a conveyor system, which can be a forming wire system 106 (i.e., a foraminous belt) moving clockwise about rollers 108. Filaments 104 may be cooled using vacuum suction applied through the forming wire system, and/or cooling fans (not shown). The vacuum can also help hold the filaments 104 against the foraminous wire system. Tackifier loading of about 23 percent has been found to be a practical limit with certain forming wires. However, it is contemplated that this percentage maybe increased with modifications to the forming wires which are designed to enhance handling of the adhesive rich fibers. The tackifier may be present in amounts for about 5 percent to about 40 percent and desirably from about 15 percent to about 25 percent.

The filaments 104 are then stretched by tensioning rollers 110 to elongate and tension the filaments. Desirably the tension rollers 110 are provided with a surface having little to no affinity for the adhesive of the filaments 104.

After the filaments 104 are stretched, they are laminated to the first facing material 112 and desirably at the same time to a second facing material 114. The first facing material 112 is unwound from a roller 116 and laminated to a first side of the filaments 104. The second facing material 114 is unwound from a second roller 118 and laminated to a second side of the filaments 104. Before the facing materials 112, 114 are laminated to the filaments 104 the facing materials may also be stretched by additional rollers (not shown). The laminate material is then passed through nip rolls 120 to bond the adhesive-surfaced elastic filaments to the facings 84, 86 by contact adhesion to produce the elastic laminate 122. The elastic laminate 122 is then allowed to relax, forming gathers therein (see FIG. 8) and collected on a collection roll 124 for further use.

As in the VFL process, the nip rollers 120 may be desirably designed to provide a 100% bond area through the use of flat calender rolls or may provide a patterned bond area. The rollers 120 can be heated to a degree below the melting points of the various laminate components, or may be ambient, or chilled.

Figure 7:
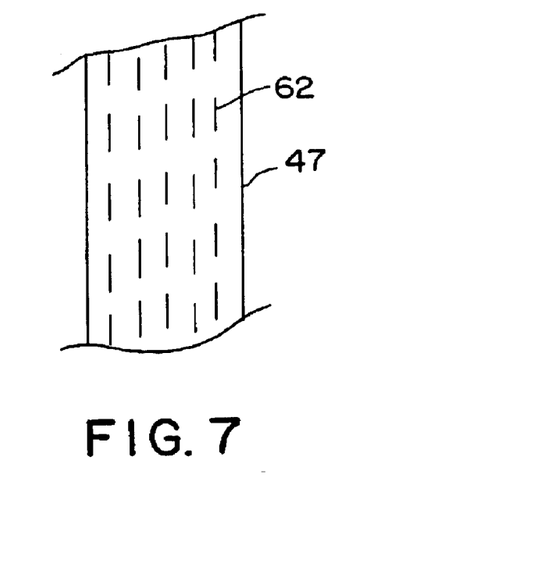
FIGS. 7 and 8 illustrate top plan views of laminates of the present invention stretched and unstretched in the longitudinal, or machine direction, respectively.
Figure 8:
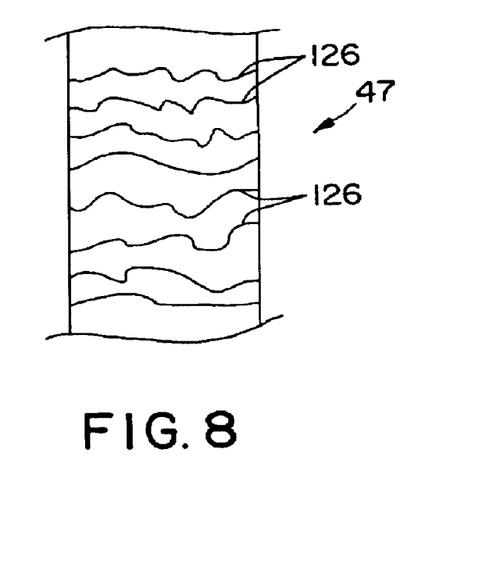

Referencing FIGS. 7 and 8, an exemplary elastic laminate material 47 appears in a stretched, or tensioned, condition in FIG. 7 showing the elastic strands, e.g. 62, in phantom. FIG. 8 shows the elastic laminate material 47 in a relaxed, or untensioned, condition with gathers 126 formed in the material 47 by the contraction of the elastic strands (not shown).

Having thus described a light weight, flexible, easily manufactured, elastic laminate of good aesthetics it will be appreciated that many variations thereon may occur to the person having ordinary skill in the art. Thus, the invention is intended to be limited only by the appended claims and not by the exemplary embodiments and aspects put forth herein.

We claim:

1. An elastic laminate, comprising:
   a) a first facing web;
   b) a second facing web;
   c) a plurality of thermoplastic elastomeric fiber strands located between the first facing web and the second facing web; and
   d) the fiber strands having an elastic core and adhesive surfaces and bonding the first facing web and the second facing web together by contact adhesion with the adhesive surfaces of the fibers to create the elastic laminate.

2. A disposable garment including the elastic web of claim 1 incorporated therein as a side panel.

3. An elastic laminate, comprising:
   a) a first web constructed to be on an interior side of a garment;
   b) a second web constructed to be on an exterior side of the garment;
   c) a plurality of thermoplastic elastomeric fibers located between the first web and the second web; and
   d) the fibers having an elastic core and adhesive surfaces and bonding the first web and the second web together by contact with the adhesive surfaces of the fibers to create the elastic laminate.

4. The elastic laminate according to claim 3 wherein the thermoplastic fibers have elastic cores which are nonadhesive.

5. The elastic laminate according to claim 3 wherein the thermoplastic fibers having a melting point over 200 degrees F.

6. The elastic laminate according to claim 3 wherein the first web is a nonwoven web of between about 0.1 osy and about 4.0 osy basis weight comprising substantially continuous spunbond polypropylene filaments.

7. The elastic laminate according to claim 3 wherein the second web is a nonwoven web of between about 0.1 osy and about 4.0 osy basis weight comprising substantially continuous spunbond polypropylene filaments.

8. The elastic laminate according to claim 3 wherein the first web is a nonwoven web.

9. The elastic laminate according to claim 3 wherein the second web is a nonwoven web.

10. The elastic laminate according to claim 4 wherein the thermoplastic fibers include a bicomponent fiber of substantially sheath/core or partial sheath/core morphology wherein a core section of the fiber is a nonadhesive elastomer and a sheath section is an adhesive.

11. The elastic laminate according to claim 5 wherein the thermoplastic fibers include a homofilament comprising a thermoplastic elastomeric polymer with a tackifier compound therein, the tackifier being concentrated at the surface of the filament to be the adhesive.

12. The elastic laminate according to claim 11 wherein the homofilament comprises an elastic block copolymer.

13. The elastic laminate according to claim 12 wherein the tackifier includes hydrogenated hydrocarbon resin tackifier.

14. The elastic laminate according to claim 10 wherein the adhesive is an elastomer/tackifier blend.

15. The elastic laminate according to claim 10 wherein the fiber is a spunbond bicomponent.

16. The elastic laminate according to claim 10 wherein the fiber is a meltblown bicomponent.

* * * * *